(12) United States Patent
Matsumoto et al.

(10) Patent No.: US 7,981,689 B2
(45) Date of Patent: Jul. 19, 2011

(54) ABSORPTION SPECTROMETRIC ANALYSIS MICROCHIP AND METHOD

(75) Inventors: Shigeki Matsumoto, Himeji (JP); Shigenori Nozawa, Himeji (JP)

(73) Assignee: Rohm Co., Ltd., Kyoto-shi, Kyoto (JP)

( * ) Notice: Subject to any disclaimer, the term of this patent is extended or adjusted under 35 U.S.C. 154(b) by 793 days.

(21) Appl. No.: 11/224,955

(22) Filed: Sep. 14, 2005

(65) Prior Publication Data

US 2006/0061760 A1 Mar. 23, 2006

(30) Foreign Application Priority Data

Sep. 22, 2004 (JP) ................................. 2004-274673

(51) Int. Cl.
*G01N 21/03* (2006.01)
(52) U.S. Cl. .......... 436/164; 436/165; 422/50; 422/401; 422/408; 422/412; 422/414; 422/63; 422/68.1; 422/82.05; 422/82.06; 422/82.09; 422/502; 422/503; 422/504; 422/507
(58) Field of Classification Search .................... 422/50, 422/82.09, 401, 408, 412, 414, 63, 68.1; 422/82.05, 82.06, 502, 503, 504, 507; 436/164, 436/165
See application file for complete search history.

(56) References Cited

U.S. PATENT DOCUMENTS

| 4,088,448 | A | 5/1978 | Lilja et al. |
| 6,537,501 | B1 * | 3/2003 | Holl et al. ..................... 422/101 |

FOREIGN PATENT DOCUMENTS

| EP | 2004-077305 | 3/2004 |
| EP | 2004-109099 | 4/2004 |
| EP | 1 489 403 A1 | 12/2004 |
| EP | 1669733 A1 | 6/2006 |
| JP | 2004-77305 A | 3/2004 |
| JP | 2004-109099 | 4/2004 |

OTHER PUBLICATIONS

Yokogawa et al, "Colorimetric Analysis Chip Checking Hepatic Functions", Oct. 5-9, 2003, 7th International Conference on Miniaturized Chemical and Biochemical Analysis Systems, p. 895-898.*
Oki et al, "Biochip which Examines Hepatic Function by Employing Colorimetric Method", Jpn. J. Appl. Phys. vol. 42 (2003), pp. L342-L345.*
Mogensen et al, "Integration of polymer waveguides for optical detection in microfabricated chemical analysis systems", Jul. 1, 2003, Applied Optics, vol. 42, No. 19, pp. 4072-4079.*
Akio Oki et al., Development of Healthcare Chips Checking Life-Style-Related Diseases, Materials Science and Engineering, vol. C24, Dec. 2004, XP004637957, pp. 837-843, Published by Elsevier B.V.

* cited by examiner

*Primary Examiner* — In Suk Bullock
*Assistant Examiner* — Dennis M White
(74) *Attorney, Agent, or Firm* — Roberts Mlotkowski Safran & Cole, P.C.; David S. Safran

(57) ABSTRACT

An absorption spectrometric analysis microchip with a chamber for holding a sample, a chamber for holding a reagent which reacts with this sample, a mixing chamber for mixing the reagent with the sample with the formation of a mixture and a sensing part with a sensing chamber for holding the mixture with a light incidence surface for the entry of light into the sensing chamber and a light exit surface for emergence of light from the sensing chamber. At least one of the light incidence surface and light exit surface is located in a recess area of the sensing part.

8 Claims, 5 Drawing Sheets

ABSORPTION SPECTROMETRIC ANALYSIS MICROCHIP AND METHOD

BACKGROUND OF THE INVENTION

1. Field of Invention

The invention relates to a microchip for executing blood analysis by an absorption spectrometric process. The invention relates especially to a microchip which is used to measure the amount of an enzyme, such as GTP (glutamyl-transpeptidase), γ-GTP or the like, and which is needed, for example, to diagnose liver function of the human body.

2. Description of Related Art

Recently μ-TAS (μ-Total Analysis System) has been considered, in which chemical analyses and the like are performed in a more precise manner using micromechanical engineering instead of a conventional device. In the case of using μ-TAS for medical fields there are the following advantages:

(1) By reducing the amount of sample, such as, for example blood, the burden on the patient can be reduced.

(2) By reducing the amount of reagent, the examination costs can be reduced.

(3) Since the device is small, the examination can be easily carried out.

It is considered that using these advantages the patient himself can carry out blood analysis at home, a blood analysis device using a microchip being used as a family specification.

In analysis by an absorption spectrometric process using a microchip, the concentration of a desired enzyme which is contained in the plasma can be measured by carrying out the series of operations described below. These operations are:

(1) Blood which was taken using a painless needle is delivered into the chip.

(2) The blood in the chip undergoes centrifugal treatment and is separated into plasma and hematocytes.

(3) The plasma and reagent are uniformly mixed with one another using a mixer and a mixture is produced therefrom.

(4) The mixture is delivered by means of a suction pump into a sensing chamber.

(5) The mixture which was delivered into the sensing chamber is irradiated with light from a light source and the attenuation of the light at a certain wavelength is measured.

A method of analyzing the concentration of an enzyme which is contained in the blood, such as, for example GTP, γ-GTP or the like, and which is needed to diagnose liver function, is disclosed, for example, in Japanese patent disclosure document JP 2004-109099 A. This publication describes a process in which light which is emitted from a light source, such as a light emitting diode or the like, which is incident from the top of the chip, which is totally reflected in an extremely small channel in the chip which is filled with an analysis sample, such as, for example, plasma, and which then emerges on the top of the chip, and is received by a detector, such as a silicon photodiode or the like.

However, the light emitted by the light emitting diode is scattered light. It is extremely difficult to cause the light incident in the chip to be totally reflected overall in an extremely small channel. Therefore, there is the disadvantage that the absorbance cannot be measured with high precision. The measurement of absorbance by the arrangement both of the light source as well as of the detector on the top of the microchip as described in the aforementioned publication causes the occurrence of measurement errors; this is not desirable.

On the other hand, Japanese patent disclosure document JP-2004-77305 A describes a process in which light from a light source can be incident from one side of a microchip, in which the light is absorbed by a sample with which an extremely small channel in the microchip is filled, and in which the transmitted light which emerges from the other side is measured. It can be imagined that, in this process, absorbance can be measured with high precision when blood is used as the sample.

In a microchip, due to its small size, there is a separate task. To measure the absorbance, a suitable extinction length is necessary. In order to keep the amount of the sample and of reagent small, there is no other method than making the area of the light incidence surface and the light exit surface in the sensing chamber extremely small.

If, in this way, the sensing chamber has a very narrow shape, the effect of the state of the light incidence surface and the light exit surface on the transmission factor in the sensing chamber is large. Since a microchip normally is made of a macromolecular material, damage easily occurs in the case of contact with a surrounding device when setting on a device for measuring the absorbance. Furthermore, there is a case in which contaminants, such as sebum, adhere to the light incidence surface and the like when the user handles it with bare hands. In this case, the absorbance cannot be exactly measured due to the adverse effect of a rough surface of the light incidence surface, resulting in the disadvantage that the concentration of the enzyme which is contained in the measurement sample cannot be exactly determined.

SUMMARY OF THE INVENTION

A primary object of the invention is to devise a microchip in which exact measurement of the absorbance can be achieved by a reduced adverse effect on the light incidence surface and the like in the sensing chamber.

In a microchip with:
a chamber for holding a sample,
a chamber for holding a reagent which reacts with this sample,
a mixing chamber for mixing the reagent with the sample to form a mixture and
a sensing chamber for holding the mixture with a light incidence surface for the entry of light into the sensing chamber and a light exit surface for emergence of light from the sensing chamber,
the above described object is achieved in that at least one of the light incidence surface and light exit surface is located in a concave area of the sensing part.

ACTION OF THE INVENTION

In a microchip in accordance with the invention, the measure that at least on one end of the lengthwise direction of the sensing chamber which is filled with a mixture, a concave area with a light incidence surface and a light exit surface is formed, reliably prevents the disadvantage that the light incidence surface and the like of the sensing chamber can be damaged and that contaminants can adhere to it. In the determination of the amount of a certain enzyme which is contained in a measurement sample, for example, in the blood, therefore, an error does not occur. As a result, it can be expected that exact analysis results will be obtained.

The invention is further described below with reference to the accompanying drawings.

DETAILED DESCRIPTION OF THE INVENTION

Figure 1:
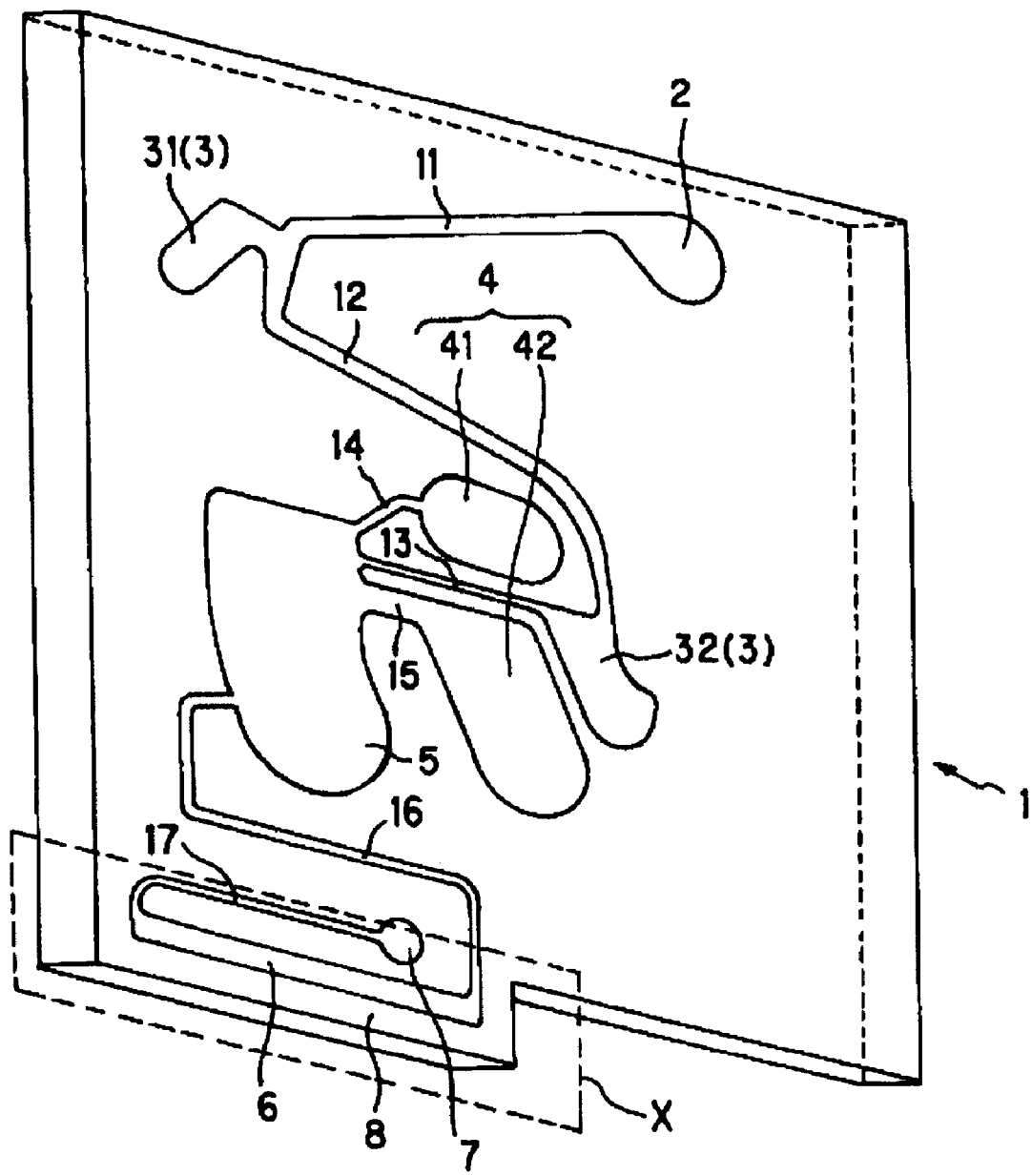
FIG. 1 is a schematic representation of a microchip in accordance with the invention.

FIG. 1 schematically shows the arrangement of a microchip in accordance with the invention. The body of the microchip 1 is produced by cementing, for example, two plate components together. One of the bonding surfaces of the plate components is formed beforehand with a groove which forms a cavity when the surfaces are cemented together. Specifically, between the plate components there are a sample chamber 3, a reagent chamber 4, a mixing chamber 5, and a mixture receiving sensing chamber 6. Furthermore, on one side of the microchip 1 there is a chamber 2 for delivering the sample, a part 7 for connection of a suction device and a sensing part 8 with opposed recesses in which mixture receiving sensing chamber 6 is located.

The chamber 2 for delivering the sample is used to deliver a sample, such as blood. It is an opening which is provided on one side of the plate component.

The sample chamber 3 is comprised of a first sample chamber 31 and a second sample chamber 32. A channel 11 leads from the first sample chamber 31 to the chamber 2 for delivering the sample, and furthermore, a channel 12 leads from the first sample chamber 31 to the second sample chamber 32. The reagent chamber 4 is comprised of a first reagent chamber 41 which is used for receiving a substrate liquid, and of a second reagent chamber 42 which is used for receiving a buffer solution. The mixing chamber 5 is used to mix the substrate liquid with the buffer solution and the sample to produce a mixture and is connected via the channels 13, 14, and 15 to the second sample chamber 32, to the first reagent chamber 41 and to the second reagent chamber 42, respectively. The mixture with which the mixing chamber 5 is filled is adequately moved in the channel 16 to then fill the filling chamber 6 with this mixture. The part 7 for connection of a suction device is the point to which is connected a suction pump (not shown) which is used to deliver the mixture by suction to the mixture filling chamber 6 and which is connected via a drain channel 17 to the mixture filling chamber 6.

The sensing part 8 which has the mixture filling sensing chamber 6 is the site at which the concentration of a desired portion contained in the mixture is measured using passage of the light from a light source, for example, a discharge lamp or the like, and by means of an absorption spectrometric process.

Figure 2:
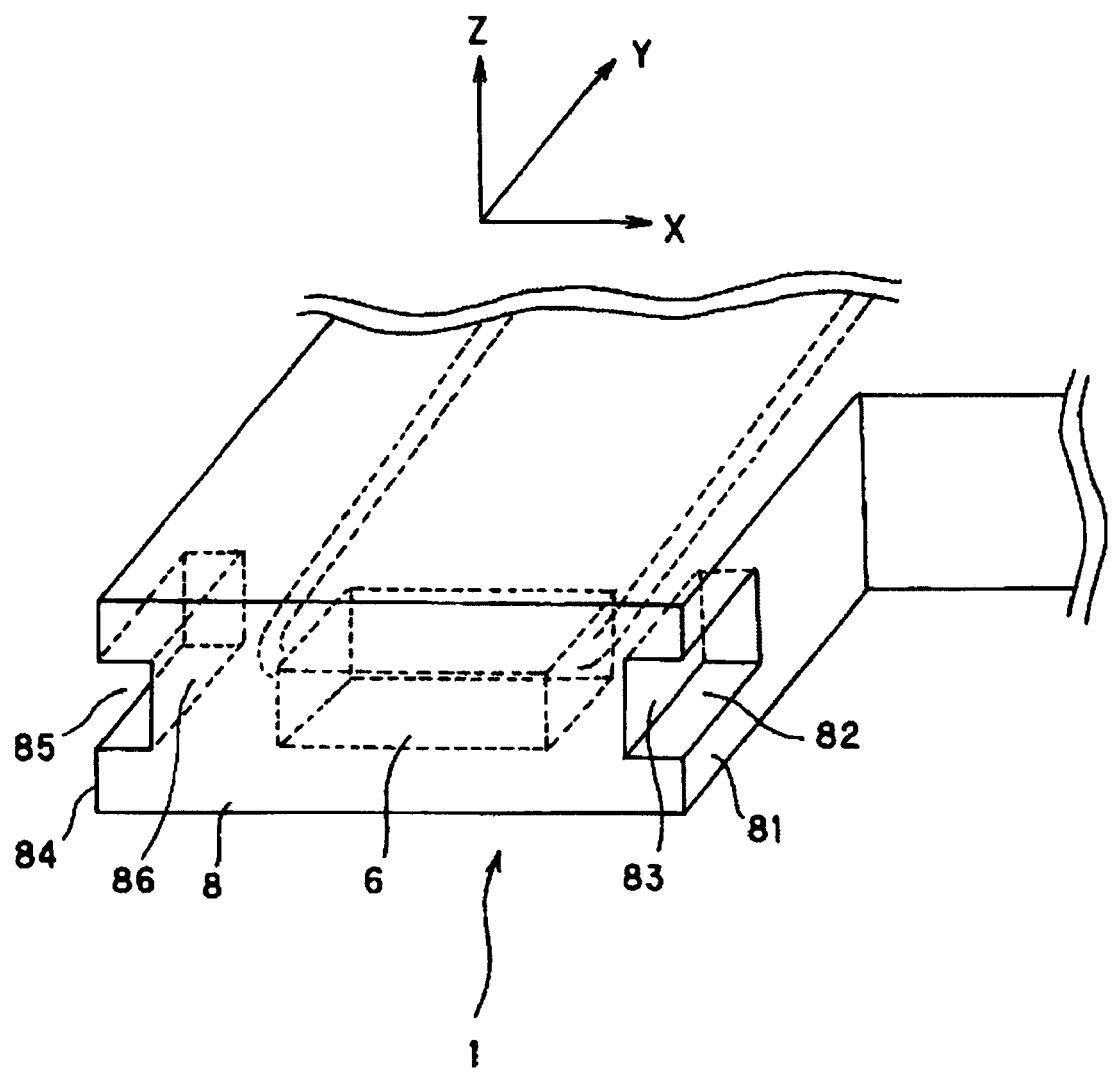
FIG. 2 is an enlargement of the detail X shown in FIG. 1.

FIG. 2 is an enlargement of the part X which, as shown in FIG. 1, is formed as a protrusion of the microchip body. The sensing part 8 has a rectangular shape which has a longitudinal axis which is essentially aligned with the optical axis. On one end face 81, a recessed part 82 is formed in which a light incidence surface 83 is formed. On the other end face 84, a recessed part 85 is formed in which a light exit surface 86 is formed. The concave part 82 and the concave part 85 are opposite one another in the direction of the optical axis.

The advantage from the arrangement of the sensing chamber 6 in the sensing part 8 of the plate component is described below. The length of the determination path (length of the optical path) differs depending on the type of reagent used. In the case, for example, of using a reagent with high absorption, it is necessary to reduce the length of the optical path. It is therefore necessary to select a microchip with a sensing chamber with a suitable length according to the type of reagent used. By the arrangement of the microchip in accordance with the invention, the length of the sensing chamber can be suitably regulated according to the type of reagent.

Figure 3:
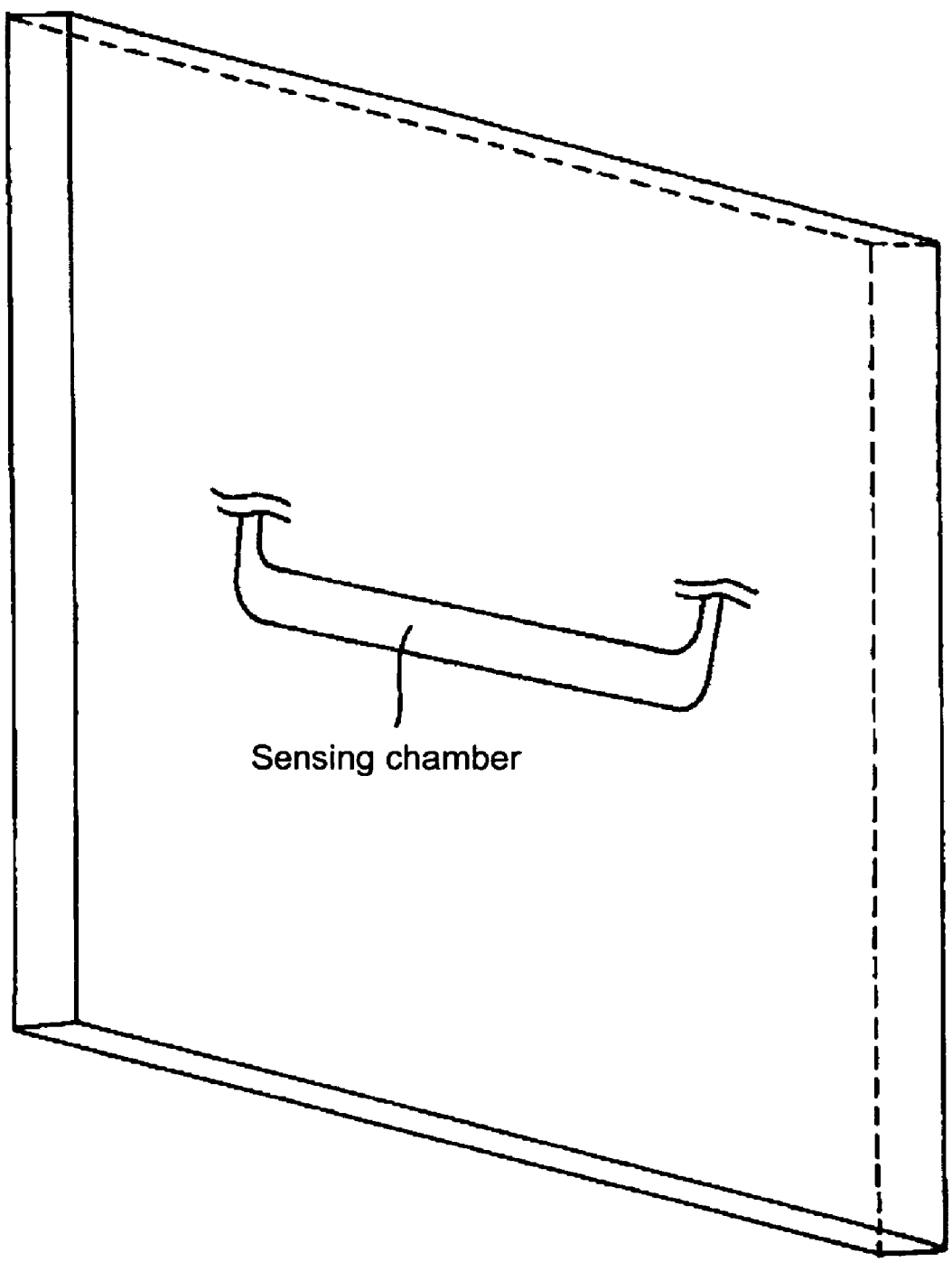
FIG. 3 is a schematic representation of a microchip in which a sensing chamber with a short total length is located in the vicinity of a plate component.

On the other hand, in the case in which a sensing chamber 6 with a small overall length for use of a reagent with high absorption is located in the manner shown in FIG. 3 in the vicinity of the middle area of the plate component, the disadvantage arises that by absorption or scattering of the light from the light source described below by the plate component, the absorbance can no longer be measured with high precision.

FIGS. 4(a) and 4(b) each show a unit for measuring the absorbance for a microchip in accordance with the invention. FIG. 4(a) shows the state in which the microchip 1 was inserted into the chip holder 10. FIG. 4(b) is a cross section cut along line A-A' as shown in FIG. 4(a).

The chip holder 10 is comprised of two components formed by division, the inside of one of the components being provided with a straight groove. By joining the two components, a capillary 11 can be easily formed in the chip holder 10. The opening diameter of the capillary 11 is smaller than the diameter of the cross section perpendicular to the optical axis of the sensing chamber 6. For example, the opening diameter of the capillary 11 is 0.3 mm and the diameter of the cross section perpendicular to the optical axis of the sensing chamber 6 is 0.7 mm. The reason that there must be such a capillary 11 is that the microchip 1 in accordance with the invention has the above described special arrangement for which there is a sensing chamber 6 in the sensing part 8 which is formed in the plate component.

The microchip 1 is inserted into the chip holder 10 such that an end of the capillary 11 is located on the light incidence surface 83. A light receiving element 14 of a silicon photodiode is located on the light exit surface 86 for determining the light which has passed from the mixture filling chamber 6 in the sensing part 8.

The light which is incident in the capillary 11 is emitted from a light source 13 and has a wavelength selected by a bandpass filter 12, passes through the capillary 11, enters the sensing chamber 6 and is received by the light receiving element 14. The light which has passed through the capillary 11 and which is incident in the sensing chamber 6 has a large proportion of parallel light and increases the accuracy of measuring the absorbance.

The light source 13 is a xenon lamp having an arc tube filled with xenon as the emission substance. Since a xenon lamp is almost a point light source and since it has the radiation characteristic that parallel light can emerge with high efficiency, it is suited as a light source for a microchip in which there is a demand for incidence of light from the light source in the extremely small area (sensing chamber 6) which is described below. Furthermore, broad light from the UV range to the visible radiation range is emitted, by which use of the light with a wavelength appropriate to the analysis sample is possible. Therefore, there is the advantage that the light source need not be changed for each analysis sample. Furthermore, the environmental burden is low since mercury is not used as the emission substance.

One example of the sequence of measuring the concentration of an enzyme contained in the blood with a microchip in accordance with the invention is described below. A process for measuring the concentration of γ-GTP is described below by way of example.

(Reagent)

Substrate fluid: GluCANA (L-γ-glutamyl-3-carboxy-4-nitroanilide) 31 mmole/l

Buffer solution: Glycyl glycine 193 mmole/l, pH 7.9 (30° C.).

(Measurement Sequence)

(1) Blood which was taken with a painless needle with a very sharp tip is delivered to the microchip 1 from the chamber 2 for delivering the sample.

(2) The first sample chamber 31 is filled with plasma which was separated by the microchip 1 having been subjected to centrifugal treatment with 6000 rpm.

(3) The second sample chamber 32 is filled with a suitable amount of plasma by the microchip 1 having been subjected to centrifugal treatment with 6000 rpm again.

Figure 5:
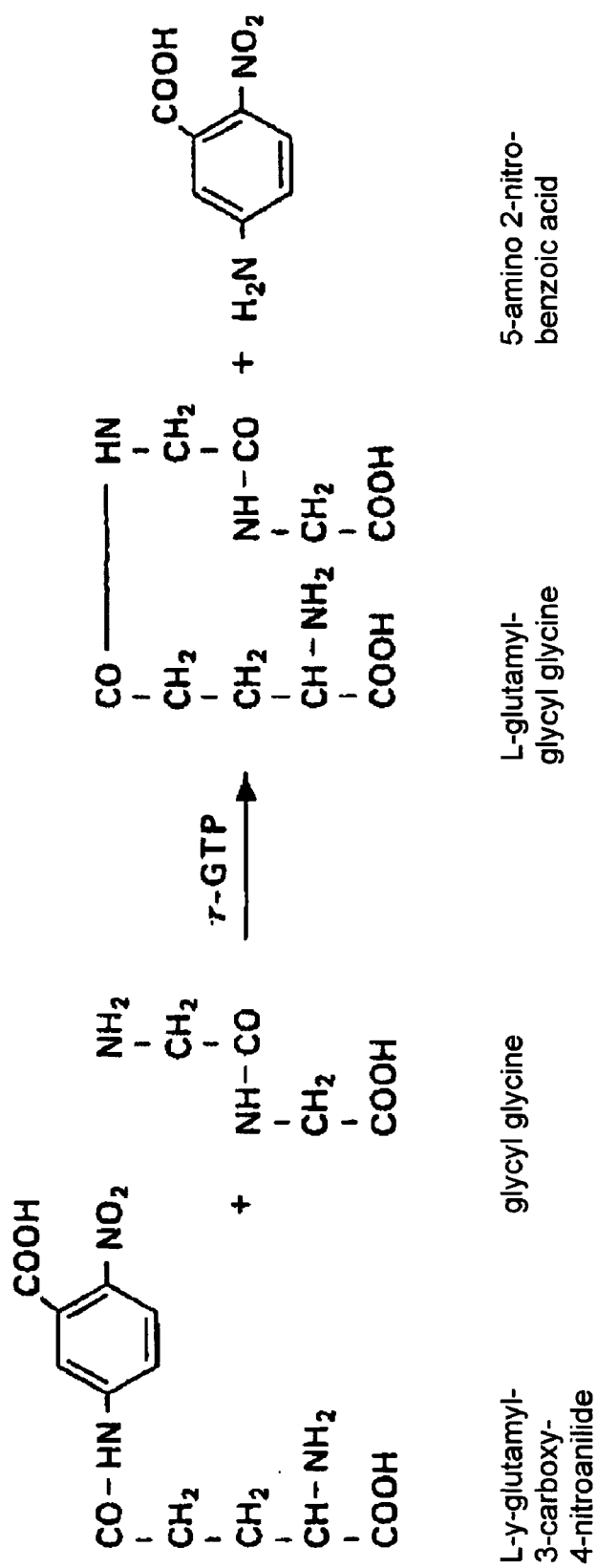
FIG. 5 is a schematic representation of the chemical reaction in a mixture.

(4) By turning the microchip 1 by 90° counterclockwise, the plasma filling the second sample chamber 32, the substrate liquid filling the first reagent chamber 41, and the buffer solution filling the second reagent chamber 42 are allowed to flow into the mixing chamber 5 where they are mixed with one another, and thus, a mixture is produced. If the above described substrate liquid and the above described buffer solution are allowed to act on the plasma, by the action of γ-GTP in the plasma, a transfer of the γ-glutamyl radical from the L-γ-glutamyl-3-carboxy-4-nitroanilide to the glycyl glycine takes place, as shown in FIG. 5. In the mixture, L-γ-glutamyl-glycyl-glycine is produced, and moreover, 5-amino-2-nitrobenzoic acid is released in the mixture.

(5) The mixture filling chamber 6 is filled with the mixture. The filling operation is carried out by connecting the suction pump to the part 7 for connection of a suction device and the sensing chamber 6 is exposed to a negative pressure.

(6) The light from the light source is passed through the sensing chamber 6. The amount of absorption of the 405 nm wavelength which is absorbed by the 5-amino-2-nitrobenzoic acid is determined. Based on this determination result, the concentration of the 5-amino-2-nitrobenzoic acid is determined by the absorption spectrometric process. The concentration of the γ-GTP in the mixture is determined via the amount of 5-amino-2-nitrobenzoic acid produced.

In the above described microchip in accordance with the invention, the recess part 82 and the recess part 85 are formed in the sensing part 8. In this way, the disadvantages that the light incidence surface and the like are damaged or impurities adhere thereto can be prevented. In a quantitative determination of the proportion of a certain enzyme which is contained in a measurement sample, such as, for example, in blood, no error occurs. Therefore, it can be expected that exact analysis results are obtained. When setting the microchip 1 on the chip holder 10, it is not necessary to be overly sensitive and careful to prevent damage to the light incidence surface and the like. Furthermore, it is also possible to work with bare hands. This improves handling.

Conversely, in an arrangement in which there is no recess part in the sensing part 8, as in a conventional microchip, it can be imagined that, by damage to the light incidence surface and the like and by adherence of impurities thereto, errors occur in the quantitative value, and therefore, an exact analysis result cannot be obtained. If the attempt is made to avoid these measurement errors, strong nerves and high concentration are necessary to prevent the light incidence surface and the like from coming into contact with a surrounding device, such as, for example, the chip holder, and being damaged, or to prevent impurities from adhering to it when the microchip is set on the device for measurement of the absorbance. The conventional arrangement is therefore not advantageous with respect to handling.

A test which was carried out to confirm the action of the invention is explained detail below.

EMBODIMENT

According to the arrangement shown in FIG. 1, a microchip 1 in accordance with the invention was produced. The arrangement of this microchip 1 is described below.

The plate components comprising the microchip 1 are made of polyethylene terephthalate (PET). Their length (including the sensing part 8) is 25 mm, the width is 25 mm and the thickness is 2 mm. The numerical values of the sensing part are described below with reference to FIG. 2. For the sensing part 8, the length (Y axis) is 2.5 mm, the width (X axis) is 12.0 mm and the thickness (Z axis) is 2 mm. For the first recess part 82, the depth (X axis) is 1 mm. For the light incidence surface 83, the length (Z axis) is 1 mm and the width (Y axis) is 2 mm. The depth (X axis) of the second concave part 85 is 1 mm. For the light exit surface 86, the length (Z axis) is 1 mm and the width (Y axis) is 2 mm.

The measurement sample is 1 μl (microliter) to 2 μl of blood. As was described above under (Reagent), 2.1 μl GluCANA was used as the substrate liquid and 8.4 μl glycyl glycine was used as the buffer solution as the reagent.

COMPARISON EXAMPLES

A microchip with the same arrangement as the microchip 1 was produced according to the embodiment except for the fact that there is no recess parts on the two end faces of the sensing part.

Figure 4:
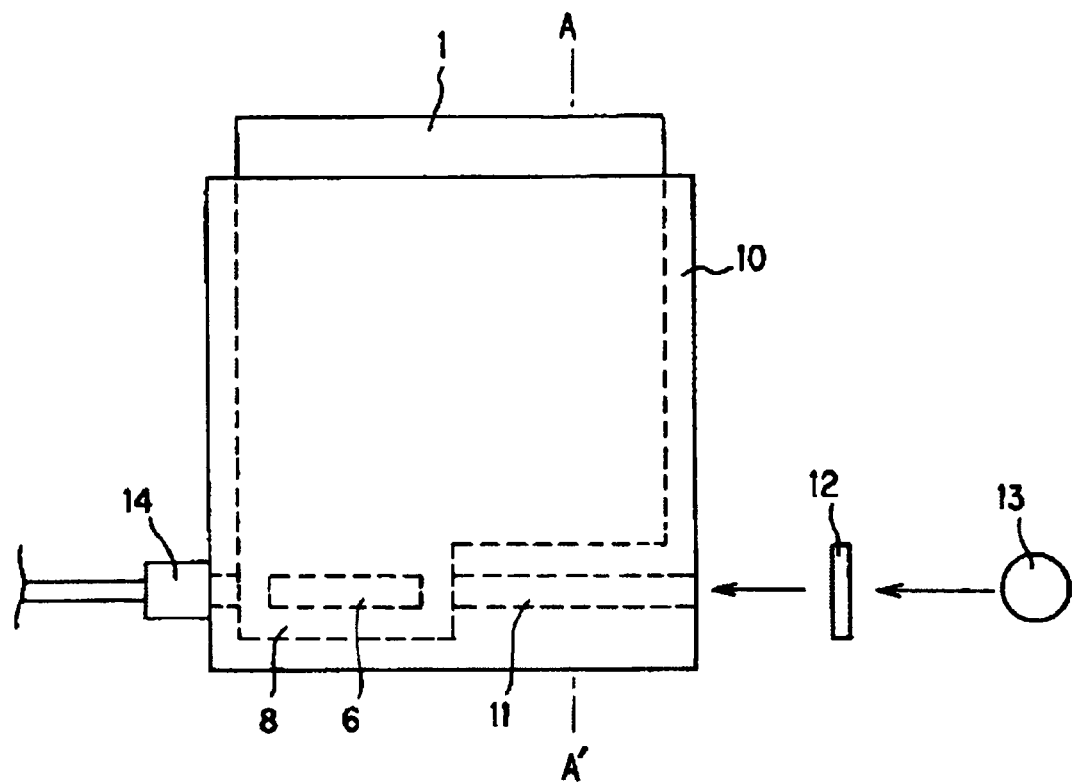
FIG. 4(a) is a schematic representation of a unit for measuring the absorbance for the microchip in accordance with the invention and FIG. 4(b) is a cross-sectional view taken along line A-A' of FIG. 4(a)
Figure 4:
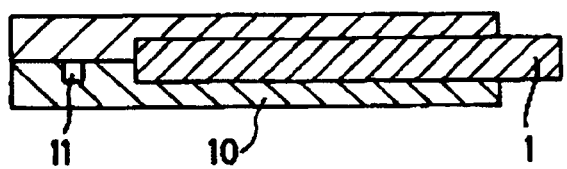

Using the produced microchip according to the embodiment and according to the comparison examples, the unit for measuring the absorbance shown in FIGS. 4(*a*) and 4(*b*) was produced. For the respective unit, light which was emitted from a xenon lamp with 75 W was allowed to be incident in the sensing chamber via the capillary, the light transmitted by the mixture filling sensing chamber was determined by means of a light receiving element and the transmission factor of the light with a wavelength 405 nm was studied. This test was carried out in the state in which the above described measurement sequence (1) to (5) was not carried out, i.e., in the state in which the mixture filling chamber was empty. Table 1 shows the results. In Table 1, the light transmission factor for comparison examples 1, 2, 3 and 4 is shown using relative values, for which the light transmission factor of the microchip according to the embodiment is indicated as 100%.

TABLE 1

|  | Transmission factor (%) |
| --- | --- |
| Embodiment | 100 |
| Comparison example 1 | 95.7 |
| Comparison example 2 | 91.4 |
| Comparison example 3 | 142.3 |
| Comparison example 4 | 121.9 |

As shown in Table 1, it becomes apparent that for the microchips according to comparison examples 1 and 2 the light transmission factor is lower than in the microchip according to the embodiment. The reason for this is presumably that the microchips according to comparison examples 1 and 2 were damaged by contact of the light incidence surfaces and the like with a surrounding device, such as, for example, a chip holder, when setting on the device for measuring the absorbance. Furthermore, it is apparent that the light transmission factor of the microchips according to comparison examples 3 and 4 is larger compared to the microchip according to the embodiment. It can be imagined that the reason for this is that, for the microchips according to comparison examples 3 and 4, impurities, such as sebum and the like, adhered to the two end faces of the sensing part and that the asperities of the two end faces of the sensing chamber (in the production of the microchips more or less asperities are formed) were smoothed.

As was described above, in the microchips according to the comparison examples an exact analysis result cannot be obtained because, as a result of damage to the light incidence surface and the like of the sensing chamber, and as a result of the impurities adhering thereto, such as sebum and the like, errors occur for the transmission factor of the light with a wavelength of 405 nm. The effectiveness of the arrangement in accordance with the invention for which there is a recessed part on the ends of sensing part was thus confirmed.

What is claimed is:

1. Absorption spectrometric analysis microchip, comprising a microchip body in which is formed:
   a chamber for holding a sample,
   a chamber for holding a reagent which reacts with the sample,
   a mixing chamber for mixing the reagent with the sample to form a mixture, and
   a sensing part having a mixture receiving sensing chamber for holding the mixture, the sensing part having a light incidence surface for the entry of light into the sensing chamber on first face thereof and a light exit surface for emergence of light from the mixture receiving sensing chamber on an opposite second face thereof,
   wherein the sensing part with the sensing chamber is located in a protrusion of the microchip body,
   wherein the light incidence surface is located in a first recess area of the sensing part and light exit surface is located in a second recess area of the sensing part, and
   wherein the sensing part has a longitudinal axis that is essentially aligned with the optical axis of the light that is directed through the sensing chamber during at least one of an absorption and a scattering of the light measurement, the first and second recesses being located opposite one another in the direction of said optical axis,
   wherein the light incidence surface is formed by a portion of the microchip body itself and is located in a first recessed area of the sensing part and the light exit surface is formed by a portion of the microchip body itself and is located in a second recessed area of the sensing part such that damage to the light incidence and exit surfaces and adherence of impurities to the light incidence and exit surfaces is prevented.

2. Absorption spectrometric analysis microchip in accordance with claim 1, wherein the light incidence surface and light exit surface are located on opposite edge areas of the protrusion of the microchip body with respect to a direction of propagation of the light.

3. Absorption spectrometric analysis microchip in accordance with claim 1, wherein each recess area comprises a recess in a respective side area of the microchip body.

4. Absorption spectrometric analysis microchip in accordance with claim 3, wherein the recess is a rectanguloidal recess.

5. Absorption spectrometric analysis microchip in accordance with claim 1, wherein said chambers are formed by facing surfaces of a pair of plate components that are bonded together.

6. Microchip in accordance with claim 1, wherein the chamber for holding a sample comprises a first and a second sample chamber which are connected to one another via a channel, wherein the chamber for holding a reagent comprises a first and a second reagent chamber, wherein the mixing chamber is connected by channels to the second sample chamber and the reagent chambers, wherein a channel leads from the mixing chamber to the mixture receiving sensing chamber, and wherein a suction channel leads out of the mixture receiving sensing chamber for connection to a suction device.

7. Absorption spectrometric analysis microchip unit, comprising, an absorption spectrometric analysis microchip, comprising a microchip body in which is formed:
   a first chamber for holding a sample,
   a second chamber for holding a reagent which reacts with the sample,
   a mixing chamber for mixing the reagent with the sample to for a mixture, and
   a sensing part having a mixture receiving sensing chamber for holding the mixture, the sensing part having a light incidence surface for the entry of light into the sensing chamber on first face thereof and a light exit surface for emergence of light from the mixture receiving sensing chamber on an opposite second face thereof,
   wherein the sensing part with the sensing chamber is located in a protrusion of the microchip body,
   wherein the light incidence surface is formed by a portion of the microchip body itself and is located in a first recess area of the sensing part and light exit surface is formed by a portion of the microchip body itself and is located in a second recess area of the sensing part, and wherein the sensing part has a longitudinal axis that is essentially aligned with an optical axis of a light source that is directed through the sensing chamber during at least one of an absorption and a scattering of the light measurement, the first and second recesses being located opposite one another in the direction of said optical axis, and
   a chip holder in which the microchip is accommodated with the light incidence surface resting against an end of a capillary passage of the chip holder and with the light exit surface resting against a light receiving component of the chip holder.

8. A method of conducting an absorption spectrometric analysis with a microchip unit in accordance with claim 7 for quantitative analysis of enzymes in blood or blood plasma comprising the steps of:
   introducing a blood sample and a reagent into said first and second chambers, respectively;
   mixing said blood sample and said reagent together in said mixing chamber;
   receiving the mixture produced by said mixing step into said sensing chamber;
   accommodating said chip into said chip holder;
   aligning an optical axis of a light source with said light incidence surface at one lateral side of the protrusion and along the longitudinal axis of said sensing part;
   introducing light from said light source into said light incidence surface in the first recess area on the first face of the sensing chamber;
   receiving light, at an opposite second lateral side of the protrusion, from said light exit surface in the second recess area on the opposite second face of the sensing chamber, and
   measuring at least one of light absorbance and scattering of the light characteristics of the received light.

* * * * *